United States Patent
Ellson et al.

(10) Patent No.: US 11,208,521 B2
(45) Date of Patent: Dec. 28, 2021

(54) THIOL-ENE PRINTABLE RESINS FOR INKJET 3D PRINTING

(71) Applicant: Inkbit, LLC, Medford, MA (US)

(72) Inventors: Gregory Ellson, Cambridge, MA (US); Wenshou Wang, Quincy, MA (US); Yan Zhang, Lowell, MA (US)

(73) Assignee: Inkbit, LLC, Medford, MA (US)

( * ) Notice: Subject to any disclaimer, the term of this patent is extended or adjusted under 35 U.S.C. 154(b) by 0 days.

(21) Appl. No.: 16/655,695

(22) Filed: Oct. 17, 2019

(65) Prior Publication Data

US 2020/0123301 A1  Apr. 23, 2020

Related U.S. Application Data

(60) Provisional application No. 62/746,730, filed on Oct. 17, 2018.

(51) Int. Cl.

| | |
|---|---|
| *C08G 18/38* | (2006.01) |
| *C08G 18/10* | (2006.01) |
| *C08G 75/02* | (2016.01) |
| *C08G 18/73* | (2006.01) |
| *B33Y 70/00* | (2020.01) |
| *C08G 18/75* | (2006.01) |
| *B29C 64/112* | (2017.01) |
| *C07C 271/24* | (2006.01) |
| *C07C 271/06* | (2006.01) |

(52) U.S. Cl.
CPC ......... *C08G 18/3876* (2013.01); *C08G 18/10* (2013.01); *C08G 18/73* (2013.01); *C08G 75/02* (2013.01); *B29C 64/112* (2017.08); *B33Y 70/00* (2014.12); *C07C 271/06* (2013.01); *C07C 271/24* (2013.01); *C08G 18/757* (2013.01)

(58) Field of Classification Search
CPC .. C08G 18/3876; C08G 18/10; C08G 18/757; C08G 75/02; C08G 18/73; B33Y 70/00; C07C 271/24; C07C 271/06; B29C 64/112

See application file for complete search history.

(56) References Cited

U.S. PATENT DOCUMENTS

| | | | | |
|---|---|---|---|---|
| 3,783,152 | A | * | 1/1974 | Larsen .................... C08G 75/12 560/26 |
| 3,931,287 | A | * | 1/1976 | Kehr .................... C07D 213/30 560/26 |
| 5,236,967 | A | * | 8/1993 | Ohkawa ............. C08F 299/022 522/100 |
| 5,270,368 | A | | 12/1993 | Lent et al. |
| 5,287,435 | A | | 2/1994 | Cohen et al. |
| 5,303,141 | A | | 4/1994 | Batchelder et al. |
| 5,889,084 | A | | 3/1999 | Roth |
| 6,492,651 | B2 | | 12/2002 | Kerekes |
| 7,300,619 | B2 | | 11/2007 | Napadensky et al. |
| 8,574,485 | B2 | | 11/2013 | Kramer et al. |
| 8,846,777 | B2 | | 9/2014 | Bowman et al. |
| 8,932,511 | B2 | | 1/2015 | Napadensky |
| 9,248,611 | B2 | | 2/2016 | Divine et al. |
| 9,347,185 | B2 | | 5/2016 | Reda |
| 9,441,084 | B2 | | 9/2016 | Heardon |
| 9,963,836 | B1 | | 5/2018 | Brenner et al. |
| 10,005,236 | B2 | | 6/2018 | Yudovin-Farber et al. |
| 10,023,500 | B2 | | 7/2018 | O'Brien et al. |
| 10,252,466 | B2 | | 4/2019 | Ramos et al. |
| 10,456,984 | B2 | | 10/2019 | Matusik et al. |
| 10,569,470 | B2 | | 2/2020 | Donovan et al. |

(Continued)

FOREIGN PATENT DOCUMENTS

| | | |
|---|---|---|
| WO | 2017/134674 A1 | 8/2017 |
| WO | 2018026829 A1 | 2/2018 |
| WO | 2018033296 A1 | 2/2018 |

OTHER PUBLICATIONS

Ligon, Samuel Clark, Robert Liska, Jürgen Stampfl, Matthias Gurr, and Rolf Mülhaupt. "Polymers for 3D printing and customized additive manufacturing." Chemical reviews 117, No. 15 (2017): 10212-10290.

Mendes-Felipe, Cristian, Juliana Oliveira, Ikerne Etxebarria, José Luis Vilas-Vilela, and Senentxu Lanceros-Mendez. "State-of-the-Art and Future Challenges of UV Curable Polymer-Based Smart Materials for Printing Technologies." Advanced Materials Technologies 4, No. 3 (2019): 1800618.

Sitthi-Amorn, Pitchaya, Javier E. Ramos, Yuwang Wangy, Joyce Kwan, Justin Lan, Wenshou Wang, and Wojciech Matusik. "MultiFab: a machine vision assisted platform for multi-material 3D printing." ACM Transactions on Graphics (TOG) 34, No. 4 (2015): 129.

(Continued)

*Primary Examiner* — Rabon A Sergent (74) *Attorney, Agent, or Firm* — Cooley LLP; Heidi A. Erlacher; Xixi Sun (57) ABSTRACT

A composition suitable for 3-D printing comprises, in one embodiment, a photopolymer including one or more thiol monomer, one or more alkene monomer, and a polymerization initiator. In another embodiment, the thiol monomer is selected from the group consisting of: glycol di(3-mercaptopropionate) [GDMP]; trimethylolpropane tris(3-mercaptopropionate) [TMPMP]; pentaerythritol tetrakis(3-mercaptopropionate) [PETMP] and 3,6-dioxa-1,8-octanedithiol [DODT]. In yet another embodiment, the alkene monomer comprises: an allyl-functional urethane/urea monomer synthesized from: an isocyanate moiety and a hydroxyl or amine functional allyl moiety. In still another embodiment, the hydroxyl or amine functional allyl moiety comprises 2-allyloxyethanol, allyl alcohol, and allylamine. In still yet another embodiment, the isocyanate moiety is selected from the group consisting of: isophorone diisocyanate (IDI), hexamethylene diisocyanate (HDI), trimethylhexamethylene diisocyanate (TMHDI), 1,3-bis(isocyanatomethyl)cyclohexane, and dicyclohexylmethane 4,4'-Diisocyanate (HMDI).

11 Claims, 4 Drawing Sheets

(56) References Cited

U.S. PATENT DOCUMENTS

| | | |
|---|---|---|
| 2002/0104973 A1 | 8/2002 | Kerekes |
| 2003/0083771 A1 | 5/2003 | Schmidt |
| 2003/0092820 A1 | 5/2003 | Schmidt et al. |
| 2003/0207959 A1 | 11/2003 | Napadensky et al. |
| 2003/0209836 A1 | 11/2003 | Sherwood |
| 2005/0023719 A1 | 2/2005 | Nielsen et al. |
| 2005/0093208 A1 | 5/2005 | Boyd et al. |
| 2007/0205528 A1 | 9/2007 | Patel et al. |
| 2010/0288194 A1 | 11/2010 | Stockwell et al. |
| 2011/0244393 A1 | 10/2011 | Ikeda |
| 2014/0027950 A1 | 1/2014 | Stockwell et al. |
| 2014/0107314 A1* | 4/2014 | Kawato .............. C08G 18/7642 528/226 |
| 2014/0239527 A1 | 8/2014 | Lee |
| 2015/0261196 A1 | 9/2015 | Wilson et al. |
| 2016/0023403 A1 | 1/2016 | Ramos et al. |
| 2016/0107383 A1 | 4/2016 | Dikovsky et al. |
| 2016/0257843 A1* | 9/2016 | Boydston .............. B29C 64/165 |
| 2016/0332381 A1 | 11/2016 | Long et al. |
| 2016/0347005 A1 | 12/2016 | Miller |
| 2016/0376453 A1 | 12/2016 | Hearon |
| 2017/0050374 A1 | 2/2017 | Minardi et al. |
| 2017/0173892 A1 | 6/2017 | Steele |
| 2017/0226267 A1* | 8/2017 | Shinohara .............. C08G 18/72 |
| 2017/0291357 A1 | 10/2017 | Fong et al. |
| 2017/0306171 A1 | 10/2017 | Vidavsky et al. |
| 2018/0009932 A1* | 1/2018 | Hearon ................... C08L 75/04 |
| 2018/0057414 A1 | 3/2018 | O'Brien et al. |
| 2018/0141268 A1 | 5/2018 | Holt |
| 2018/0148380 A1 | 5/2018 | Eckel et al. |
| 2019/0039321 A1 | 2/2019 | Matzner et al. |
| 2019/0283316 A1 | 9/2019 | Rolland et al. |
| 2019/0322031 A1 | 10/2019 | Kritchman |
| 2019/0389139 A1 | 12/2019 | Wu et al. |
| 2020/0115490 A1* | 4/2020 | Dove ................. C08G 18/8166 |
| 2020/0156298 A1 | 5/2020 | Jessen et al. |
| 2020/0338832 A1 | 10/2020 | Wang et al. |

OTHER PUBLICATIONS

U.S. Appl. No. 17/031,212, filed Sep. 24, 2020, Twiddy et al.

Sertoglu, K. (May 26, 2020) "Hybrid Manufacturing Technologies to 3D Print Parts With 'Injection Molding Quality'" 3D Printing Industry [online], Retreived Sep. 23, 2020 from https://3dprintingindustry.com/news/hybrid-manufacturing-technologies-to-3d-print-parts-with-injection-molding-quality-171991.

Wikipedia "Reaction injection molding" [online] (retrieved on Sep. 23, 2020 from https://en.wikipedia.org/w/index.php?title=Reaction_injection_molding&oldid=964596773); 2 printed pages.

* cited by examiner

THIOL-ENE PRINTABLE RESINS FOR INKJET 3D PRINTING

CROSS-REFERENCE TO RELATED APPLICATIONS

This application claims the benefit of U.S. Provisional Application No. 62/746,730, filed Oct. 17, 2018, which is incorporated herein by reference.

FIELD OF THE INVENTION

The invention relates generally to 3D inkjet printing and more specifically to the printable compositions used in a 3D inkjet printer.

BACKGROUND OF THE INVENTION

Additive manufacturing is a set of methods that allows objects to be fabricated via selective addition of material. A typical additive manufacturing process works by slicing a digital model (for example, represented using a stereolithography file (STL)) into a series of layers. The layers are sent to a fabrication apparatus that deposits the layers one by one from the bottom to the top. Additive manufacturing is rapidly gaining popularity in a variety of markets including automotive, aerospace, medical devices, pharmaceuticals, and industrial tooling.

The growth of additive manufacturing processes has led to various iterations of such processes being commercialized, including extrusion processes, such as fused deposition Modeling® (FDM®), light polymerization processes, such as stereolithography apparatus (SLA) and multijet/polyjet, powder bed fusion processes, such as selective laser sintering (SLS) or binder jetting, and lamination processes, such as laminated object manufacturing (LOM). Nevertheless, despite this growth and rapid progress, additive manufacturing has limitations, such as the materials that can be used in conjunction with such processes. There are limited types of materials, and the performance of the materials limit the efficiency and quality of the resulting object.

Inkjet 3D printing is a method of additive manufacturing where printheads deposit droplets of liquid printable resins. Printheads are typically mounted on a gantry system to allow deposition of printable resins in different locations of the build volume. The build platform may also move with respect to the printheads, which may be stationary. The liquid printable resin is solidified using UV or visible light radiation.

Multiple printheads can be used in one system in order to build objects with multiple base materials. For example, materials that have different optical, mechanical, thermal, and electromagnetic properties can be used. These materials can be combined to achieve composite materials with a wide range of properties.

The UV-curing unit is typically one of the subsystems used within an inkjet additive manufacturing apparatus. UV radiation provides the means of solidifying printable resins via photo-initiation of the polymerization reaction. UV radiation can be supplied by a variety of different mechanisms such as arrays of LEDs and Mercury or Xenon arc lamps. UV-curing is typically applied after each printed layer or after depositing each material within a layer. The UV-curing unit can be fixed with respect to the printer or it can move independently with respect to the object.

Alternatively, printable resin solidification can be achieved by changes in thermal conditions. For example, a liquid material solidifies as its temperature is lowered. A variety of different printable resins can be used in this category, such as waxes. Both UV-phase change and thermal-phase change printable resins can be combined to manufacture an object.

When manufactured using an inkjet process, 3D printed objects may need structural support. For example, most objects with overhangs need support structures. Typically, additional print data is generated for these support structures. In inkjet additive manufacturing, typically a separate printable resin is designated as a support material. This printable resin is deposited also using printheads and solidified. It is desirable for the support material to be easily removed after the print is completed. There are many potential support materials, including UV-curable materials that are soluble in water or other solvents, or wax-based materials that can be removed by melting.

After the printing process is completed, parts are typically post-processed. For example, support material may need to be removed. The parts might also need to be post-processed to improve their mechanical or thermal properties. This may include thermal treatment and/or additional UV exposure.

Printable resins suitable for inkjet printing need to conform to certain specifications. The key requirements include: 1) viscosity typically needs to be within 3-15 cps at the operating conditions; 2) surface tension typically should be between 20-45 mN/m; 3) thermal stability—the printable resin should not solidify within the printhead, printable resin container, or feeding system; 4) formulation stability—different components of the printable resin should not separate for a reasonably long time. Printable resins are typically optimized in order to meet the specifications for printing.

Furthermore, the waveform for driving the printheads must be optimized and adapted for each printable resin. Moreover, many different parameters of the printing process need to be adapted for individual printable resins, such as printhead and printable resin pre-heating.

In many cases, printable resins may include additives. These additives include colorants in the form of dyes or pigments or the mixture of pigments and dyes that are dispersed or dissolved in the printable resin. Surfactants may also be used to adjust the surface tension of the printable resin for improved jetting or printing performance. In addition, other types of particles or additives may be used in order to enhance the mechanical, thermal or optical characteristics of the cured resin.

Most currently available photo-curable printable resins for inkjet 3D printers are based on (meth)acrylate chemistry. (Meth)acrylates are popular due to a wide variety of available monomers and oligomers, low cost, and rapid cure rate. Resins ranging from soft elastomers to hard, brittle materials are available for use. However, acrylate-based materials are often unsuitable for applications requiring high stiffness, thermal resistance, or dimensional stability.

Acrylic photopolymers cure via a radical mediated chain growth mechanism. As a result, acrylic photopolymers will gel at low degrees of cure. Full cure is difficult to achieve and leads to significant shrinkage and warping as the degree of cure increases. This becomes more severe as lower-functionality acrylic monomers are used, which are necessary to achieve materials with high extensibility. Acrylate-functionalized high molecular weight oligomers may be used to make tough, elastic materials at the expense of large increases of the viscosity of the uncured resin. Thus, it is very challenging to formulate acrylic photopolymers that are processable in 3D printing systems, yet still cure at high degrees of conversion into tough, highly extensible materials.

Thiol-ene chemistry is a well-known reaction scheme in which a thiol will add to an unsaturated carbon-carbon bond. This reaction has been used to develop photopolymer resins for applications such as dental cement and implantable medical devices. Polymerization may take place under radical or basic conditions, although the radical reaction is faster by several orders of magnitude.

What is needed is a printable material that has increased strength relative to that of the readily available allyl monomers. The present invention addresses this need.

SUMMARY OF THE INVENTION

Although thiol-enes are well-known, for a variety of reasons, their use in jetted inks is not. Thiol-ene resins cure via a step-growth mechanism and are significantly less sensitive to oxygen inhibition than acrylic photopolymers. This step-growth polymerization delays the gel point in comparison to chain-growth reactions. Combined with lower oxygen sensitivity, this causes thiol-ene photopolymers to cure to higher degrees of conversion than acrylic photopolymers while displaying significantly less shrinkage and warping. This also provides more precise control over the polymer crosslink density, allowing resins with high elongation and elasticity at low viscosities. However, merely substituting thiol-ene based materials for more conventional photo-curable printable resins such as acrylic photopolymers for inkjet 3D printers will not generally provide a useful jetted ink for 3D printers. Because a thiol-ene resin for ink jet printing requires lower viscosities than other photopolymer 3D printing methods, it is only through careful formulation of particular compositions and reaction characteristics will one realize thiol-ene resins that are suitable and useful in the UV inkjet 3D printing space.

There are a wide range of commercially available thiol and alkene monomers and oligomers suitable for use in 3D deposition of printable resins. One of the primary providers of thiol monomers is Bruno Bock Thiochemicals (Eicholzer Straße 23, 21436 Marschacht, Germany), which manufactures a wide range of thiol-functional materials. Example monomers that are useful for photopolymer resins are glycol di(3-mercaptopropionate) [GDMP], trimethylolpropane tris (3-mercaptopropionate) [TMPMP], and pentaerythritol tetrakis(3-mercaptopropionate) [PETMP]. Other monomers, such as 3,6-dioxa-1,8-octanedithiol [DODT] produced by Arkema Inc. (900 First Avenue, King of Prussia, Pa., USA) are also suitable as monomers. Costs for these monomers are competitive with prices for acrylic monomers and oligomers.

Many types of suitable alkene monomers can be polymerized with thiols, such as acrylates, vinyls, allyls, and norbornenes. The polymerization kinetics, stability, and properties vary widely based on the particular type of alkene monomer that is used in the resin. Generally, the stability of the mixed resin is inversely proportional to the electron deficiency of the alkene. Highly electron-deficient alkenes such as vinyls are less stable with thiols than more electron-rich allyl monomers. Polymer homogeneity has a similar relationship, as electron-deficient alkenes will have a higher tendency to homopolymerize upon curing instead of stoichiometrically reacting with thiols. As a result, allyl-functional monomers tend to have better stability with thiols while retaining high reaction rates and cure homogeneity. Resins stabilized using phosphonic acid and radical inhibitors can have pot life similar to that of acrylic resins.

By carefully selecting the composition materials for the inkjet 3D formulation, a composition that is stable over long periods of time, with relatively low viscosity and that has a desirable mode of polymerization can result in an ink that is suitable for 3-D printing. Furthermore, elastomeric materials have not, in general, been used in 3D printing. However, with feedback approaches, such as described in U.S. Pat. No. 10,456,984 and US 2016/0167306, both of which are incorporated by reference, may be desirable and attainable with the above-described properties.

One aspect of the invention is composition suitable for 3-D printing. In one embodiment, the composition comprises a photopolymer comprising one or more thiol monomer, one or more alkene monomer, and a polymerization initiator. In another embodiment, the thiol monomer is selected from the group consisting of: glycol di(3-mercaptopropionate) [GDMP]; trimethylolpropane tris(3-mercaptopropionate) [TMPMP]; pentaerythritol tetrakis(3-mercaptopropionate) [PETMP] and 3,6-dioxa-1,8-octanedithiol [DODT]. In yet another embodiment, the alkene monomer comprises: an allyl-functional urethane/urea monomer synthesized from an isocyanate moiety and a hydroxyl or amine functional allyl moiety. In still another embodiment, the hydroxyl or amine functional allyl moiety comprises 2-allyloxyethanol, allyl alcohol, and allylamine. In still yet another embodiment, the isocyanate moiety is selected from the group consisting of: isophorone diisocyanate (IDI), hexamethylene diisocyanate (HDI), trimethylhexamethylene diisocyanate (TMHDI), 1,3-bis(isocyanatomethyl)cyclohexane, and dicyclohexylmethane 4,4'-Diisocyanate (HMDI).

BRIEF DESCRIPTION OF THE DRAWINGS

The structure and function of the invention can be best understood from the description herein in conjunction with the accompanying figures. The figures are not necessarily to scale, emphasis instead generally being placed upon illustrative principles. The figures are to be considered illustrative in all aspects and are not intended to limit the invention, the scope of which is defined only by the claims.

DESCRIPTION OF A PREFERRED EMBODIMENT

In brief overview, the invention relates to the composition of a new 3D printable material comprising allyl urethanes that have increased strength upon curing.

As will be described in greater detail below, compositions were formulated with essentially two functionality groups resulting in a material that acts as a chain extender (small amount of tri-functional monomer was added to crosslink the material). Thus, the polymer chain of the material is longer and does not connect to other polymer chains. This characteristic is particularly important for elastomeric materials, which are desired to be more stretchable, rather than more rigid. Such compositions will provide materials that have relatively low viscosity, desirable polymerization characteristics, better curing properties and with increased stability over longer periods of time.

Urethane bonds have high degrees of hydrogen bonding due to containing both a proton donor and acceptor. Incorporation of urethane bonds into acrylic photopolymers is method of increasing toughness by increasing the degree of hydrogen bonding in the cured resin. Therefore, one method for increasing the toughness of thiol-ene photopolymer resins is to synthesize monomers or oligomers which contain urethane bonds.

Figure 1:
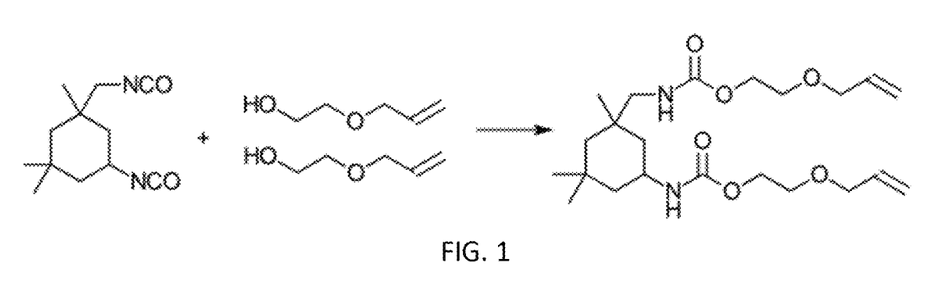
FIG. 1 is a depiction of the synthesis reaction of the di(2-allyloxyethyl carbamate) ester of isophorone diisocyanate.

In one embodiment, allyl-functional urethane monomers are synthesized by the stoichiometrically balanced reaction between di-functional isocyanate monomers such as, but not limited to, isophorone diisocyanate (IDI), hexamethylene diisocyanate (HDI), trimethylhexamethylene diisocyanate (TMHDI), 1,3-bis(isocyanatomethyl)cyclohexane, dicyclohexylmethane 4,4'-Diisocyanate (HMDI), or N,N',N"-Tris (6-isocyanatohexyl)isocyanurate and a hydroxyl or amine functional allyl monomer such as, but not limited to, 2-allyloxyethanol, allyl alcohol, and allylamine with or without the presence of a suitable catalyst such as, but not limited to, dibutyltin dilaurate (DBTDL). The reaction may be accelerated by heating, although temperatures above 70° C. risk the generation of undesirable side products. A representative reaction product between IDI and 2-allyloxyethanol is shown in FIG. 1.

Figure 2:
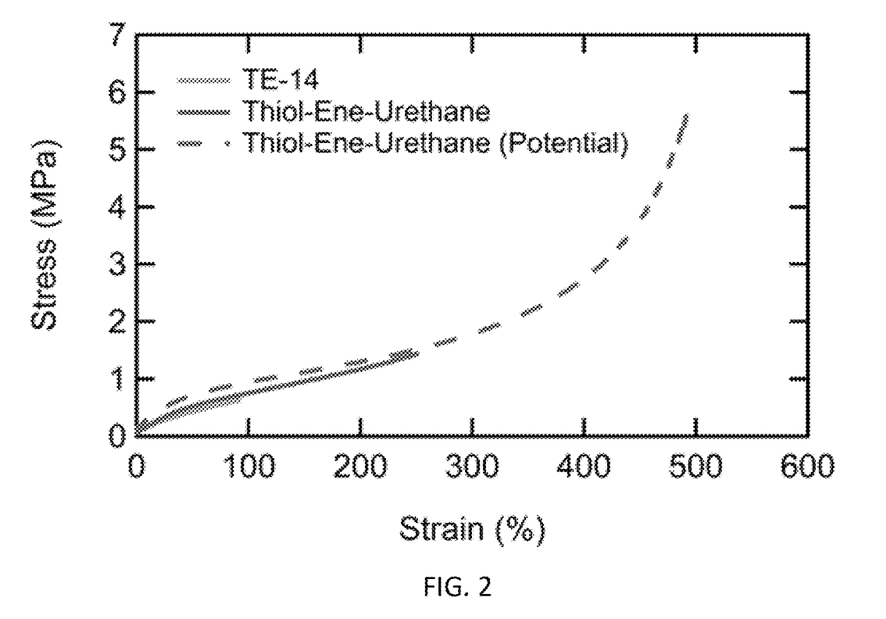
FIG. 2 is a graph of the tensile stress-strain behavior of thiol-ene printable resins made using commercial allyl monomers and synthesized allyl urethane monomers.

Such allyl urethanes are shown to significantly improve the tensile strength and maximum elongation without breaking of thiol-ene resins in comparison to printable resins made with commercially available allyl monomers and oligomers. Uniaxial tensile tests for cured thiol-ene resins containing commercial allyl monomers and the above-synthesized allyl urethane monomer are shown in FIG. 2. The tensile strength of the allyl urethane material is approximately 10 times higher and the elongation is 5 times higher than the commercial allyl material.

Figure 3:
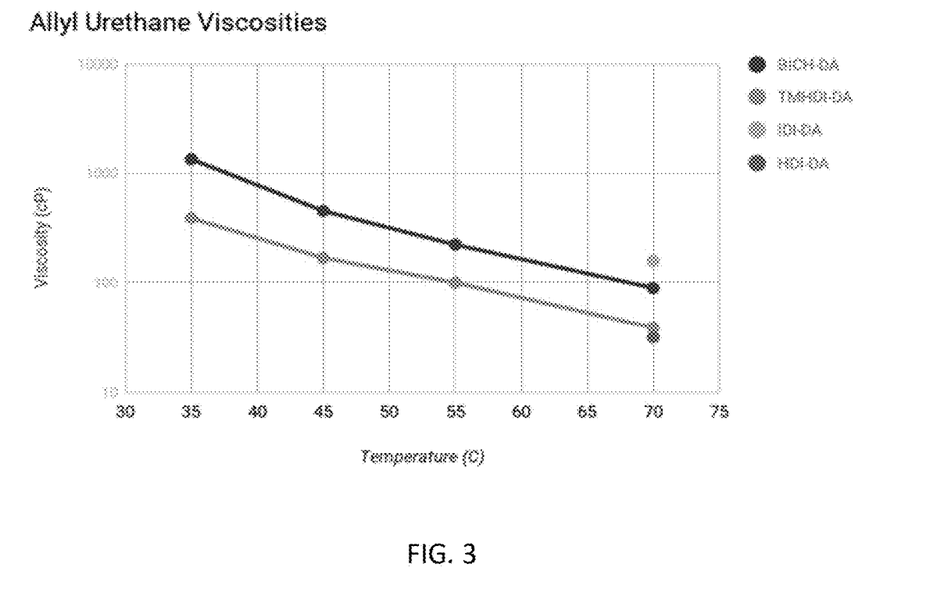
FIG. 3 is a graph of the viscosity-temperature profiles of various synthesized allyl urethane monomers.
Figure 4:
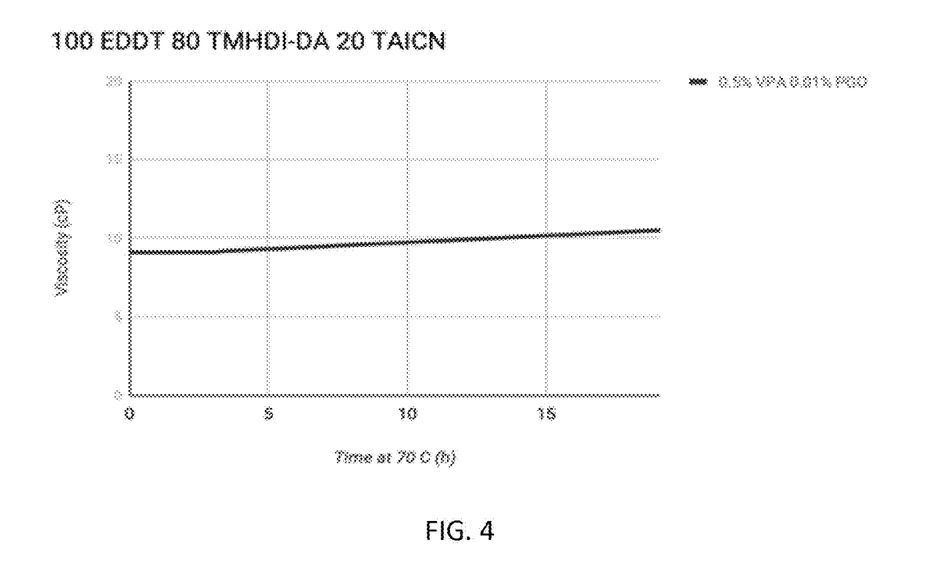
FIG. 4 is a graph of the viscosity of a thiol-ene printable resin utilizing an allyl urethane monomer at 70° C. over an 18 hour period.
Figure 5A:
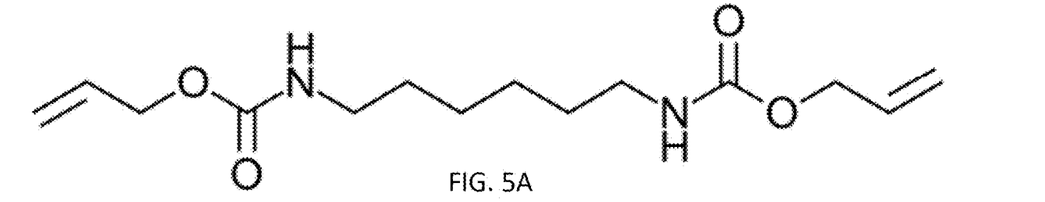
FIGS. 5A-5F depict preferred embodiments of allyl urethane/urea monomers. HDI and TMHDI are reacted with allyloxyethanol, allyl alcohol, or allylamine
Figure 5B:
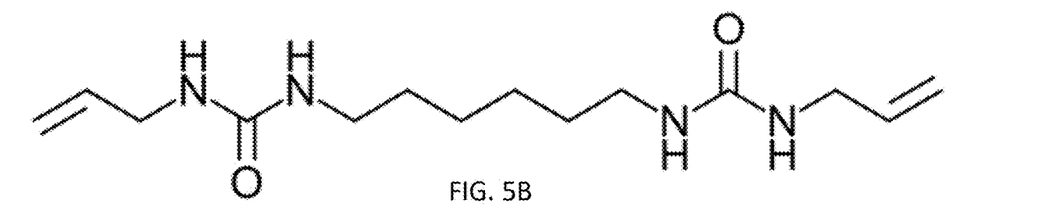
Figure 5C:
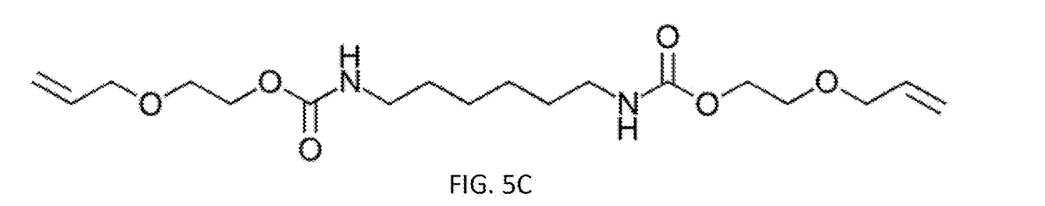
Figure 5D:
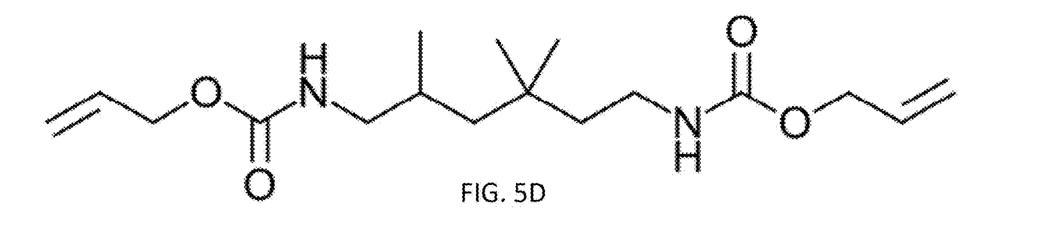
Figure 5E:
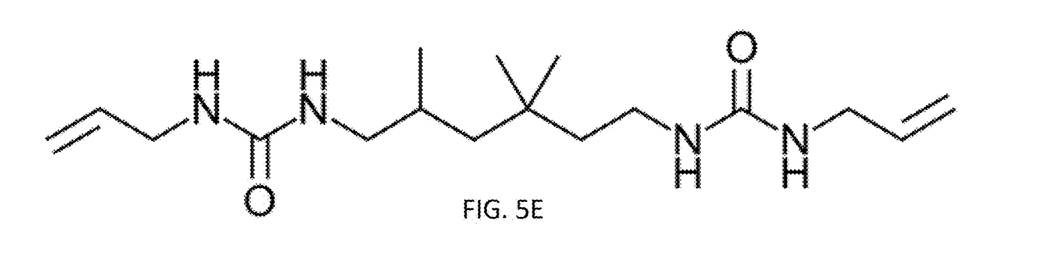
Figure 5F:
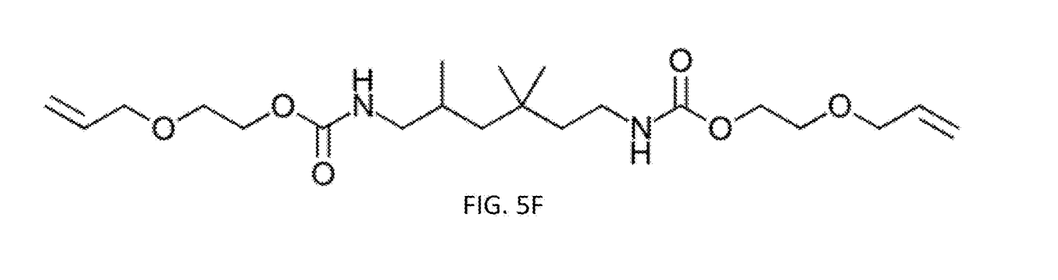

Printable resins for use in inkjet printing require that the viscosity conform to certain specifications. The viscosity of the printable resins is highly dependent on the formulation and structure of the synthesized allyl monomer. The temperature-dependent viscosity of the raw allyl monomers are shown in FIG. 3. Viscosity decreases as the monomer becomes less sterically hindered, although monomers with too little hindrance are subject to crystallization at lower temperatures. None of the monomers measured thus far demonstrate viscosities less than 30 cP, although resin viscosities in the jettable range are achievable when mixed with thiol and/or alkene monomers. An embodiment of a printable resin comprising TMHDI-DA is shown in FIG. 4 with a viscosity in the range of 10 cP at 70° C. The viscosity remains in this range over the course of one day at 70° C.

Viscosity measurements in which an isocyanate-functional monomer, trimethylhexamethylene diisocyanate (TMHDI), is reacted with three different alcohol or amine functional allyl monomers is shown in Table 1 below.

TABLE 1

| Temperature | TMHDI-Allyl Alcohol | TMHDI-Allyloxy Ethanol | TMHDI-Allyl Amine |
|---|---|---|---|
| 30 C. | 1466.0 | 817.4 | Not Measurable (High) |
| 40 C. | 608.2 | 383.8 | Not Measurable (High) |
| 50 C. | 261.3 | 190.0 | Not Measurable (High) |
| 60 C. | 129.3 | 104.4 | Not Measurable (High) |
| 70 C. | 70.3 | 61.8 | Not Measurable (High) |

*Viscosity in cP

The same adducts with hexamethylene diisocyanate (HDI) instead of trimethylhexamethylene diisocyanate (TMHDI) are solids and would require a fully heated feed system for printing.

Table 2 provides an embodiment of the composition of a printable resin comprising Glycol di(3-mercaptopropionate) (GDMP), Trimethylhexamethylene di(2-allyloxyethyl carbamate) (TMHDI-DA), Trimethylolpropane diallyl ether (TMPDAE) and Triallyl cyanurate (TAC).

TABLE 2

| Material Name | Weight Fraction (%) |
|---|---|
| Glycol di(3-mercaptopropionate) | 41.93 |
| Trimethylolpropane diallyl ether | 1.89 |
| Trimethylhexamethylene di(2-allyloxyethyl carbamate) | 47.41 |
| Triallyl cyanurate | 8.77 |
| Pyrogallol | 0.05 |
| Ebecryl 168 | 0.5 |
| Omnirad 819 | 1.0 |

Table 3 provides a list of mechanical properties, the applicable standards, and the measurements performed on the composition of a printable resin comprising Glycol di(3-mercaptopropionate) (GDMP), Trimethylhexamethylene di(2-allyloxyethyl carbamate) (TMHDI-DA), Trimethylolpropane diallyl ether (TMPDAE) and Triallyl cyanurate (TAC) shown in Table 2

TABLE 3

| MECHANICAL PROPERTIES | STANDARD | VALUE | UNIT |
|---|---|---|---|
| Ultimate Tensile Strength | ASTM D412 | 1.11 ± 0.05 | MPa |
| Elongation at Break | ASTM D412 | 256.25 ± 4.95 | % |
| Young's Modulus | ASTM D412 | 0.38 ± 0.01 | MPa |
| Tear Propagation Strength | ASTM D624-B | 3.68 ± 0.16 | kN/m |
| Shore Hardness | ASTM D2240 | 25 | Shore A |

Table 4 provides an embodiment of the composition of a printable resin comprising a thiol-ene elastomer using the TMHDI-Allyl alcohol adduct

TABLE 4

| Material Name | Weight Fraction (%) |
|---|---|
| 3,6-dioxa-1,8-octanedithiol | 36.41 |
| TMHDI-Allyl Alcohol | 61.93 |
| Triallyl isocyanurate | 1.66 |
| Pyrogallol | 0.05 |

TABLE 4-continued

| Material Name | Weight Fraction (%) |
|---|---|
| Ebecryl 168 | 0.5 |
| Omnirad 819 | 1.0 |

Table 5 provides a list of mechanical properties, the applicable standards, and the measurements performed on the composition of a printable resin for the thiol-ene elastomer using the TMHDI-Allyl alcohol adduct shown in Table 4.

TABLE 5

| MECHANICAL PROPERTIES | STANDARD | VALUE | UNIT |
|---|---|---|---|
| Ultimate Tensile Strength | ASTM D412-C | 3.97 ± 0.06 | MPa |
| Elongation at Break | ASTM D412-C | 914 ± 26 | % |
| Elastic Modulus @ 100% | ASTM D412-C | 0.3 ± 0.15 | MPa |
| Tear Propagation Strength | ASTM D624-B | 6.26 ± 0.25 | kN/m |
| Shore Hardness | ASTM D2240 | 28 | Shore A |

The disclosed composition has a number of advantages over the current state of the art such as: (1) increased tensile strength, (2) increased elongation at break, (3) low susceptibility to oxygen inhibition, (4) low shrinkage and warping, and (5) high monomer conversion. These properties are highly desirable when considering materials for use in functional 3D printed parts, especially for medical applications.

Referring to FIGS. 5A-5F, other embodiments are possible in which the photopolymer includes thiol monomers selected from the group consisting of: glycol di(3-mercaptopropionate) [GDMP]; trimethylolpropane tris(3-mercaptopropionate) [TMPMP]; pentaerythritol tetrakis(3-mercaptopropionate) [PETMP] and 3,6-dioxa-1,8-octanedithiol [DODT]. Further, the allyl-functional urethane monomer in other embodiments is synthesized from a di-functional isocyanate monomer selected from the group consisting of: isophorone diisocyanate (IDI), hexamethylene diisocyanate (HDI), trimethylhexamethylene diisocyanate (TMHDI), 1,3-bis(isocyanatomethyl)cyclohexane, and dicyclohexylmethane 4,4'-Diisocyanate (HMDI) and a hydroxyl or amine functional allyl monomer selected from the group consisting of 2-allyloxyethanol, allyl alcohol, and allylamine.

A number of implementations have been described. Nevertheless, it will be understood that various modifications may be made without departing from the spirit and scope of the disclosure. For example, various forms of the materials shown above may be used, with steps re-ordered, added, or removed. Accordingly, other implementations are within the scope of the following claims.

The examples presented herein are intended to illustrate potential and specific implementations of the present disclosure. The examples are intended primarily for purposes of illustration of the invention for those skilled in the art. No particular aspect or aspects of the examples are necessarily intended to limit the scope of the present invention.

The figures and descriptions of the present invention have been simplified to illustrate elements that are relevant for a clear understanding of the present invention, while eliminating, for purposes of clarity, other elements. Those of ordinary skill in the art may recognize, however, that these sorts of focused discussions would not facilitate a better understanding of the present disclosure, and therefore, a more detailed description of such elements is not provided herein.

Unless otherwise indicated, all numbers expressing lengths, widths, depths, or other dimensions and so forth used in the specification and claims are to be understood in all instances as indicating both the exact values as shown and as being modified by the term "about." As used herein, the term "about" refers to a ±10% variation from the nominal value. Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Any specific value may vary by 20%.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

It will be appreciated by those skilled in the art that various modifications and changes may be made without departing from the scope of the described technology. Such modifications and changes are intended to fall within the scope of the embodiments that are described. It will also be appreciated by those of skill in the art that features included in one embodiment are interchangeable with other embodiments; and that one or more features from a depicted embodiment can be included with other depicted embodiments in any combination.

What is claimed is:

1. A composition comprising:
   3,6-dioxa-1,8-octanedithiol (DODT), and one or more alkene monomer being selected from:

-continued

, and

.

2. The composition of claim 1, wherein the one or more alkene monomer is selected from:

,

,

, and

.

3. The composition of claim 1, wherein the alkene monomer is

.

4. The composition of claim 1, wherein the alkene monomer is

6. The composition of claim 1, wherein the alkene monomer is

7. The composition of claim 1, wherein the alkene monomer is

8. The composition of claim 1, wherein the alkene monomer is

9. The composition of claim 1, further comprising a polymerization initiator.

10. A cured composition being prepared by a method comprising curing the composition of claim 1.

11. The cured composition of claim 10, wherein the composition is cured by UV or visible light irradiation.

* * * * *